United States Patent [19]

Huibers

[11] 4,421,568
[45] Dec. 20, 1983

[54] PROCESS FOR MAKING L-SUGARS AND D-FRUCTOSE

[75] Inventor: Derk T. A. Huibers, Pennington, N.J.

[73] Assignee: Hydrocarbon Research, Inc., Lawrenceville, N.J.

[21] Appl. No.: 296,403

[22] Filed: Aug. 26, 1981

[51] Int. Cl.³ .................. C07H 3/02; C13K 13/00; C13D 3/02
[52] U.S. Cl. .................................. 127/48; 127/30; 127/46.1; 127/50; 435/105; 435/823
[58] Field of Search ................. 127/30, 48, 58, 42, 127/49, 50, 46.1; 435/105, 148, 94, 822, 823, 813; 536/1; 568/863

[56] References Cited

U.S. PATENT DOCUMENTS

| | | | |
|---|---|---|---|
| 1,833,716 | 11/1931 | Kluyver et al. | 435/148 |
| 2,121,533 | 6/1938 | Wells et al. | 435/823 X |
| 2,207,768 | 7/1940 | Weijlard et al. | 435/823 X |
| 2,421,612 | 6/1947 | Gray | 435/823 X |
| 3,206,375 | 9/1965 | Kinoshita et al. | 435/823 X |
| 4,029,878 | 6/1977 | Kruse | 536/1 |
| 4,173,514 | 11/1979 | Kruse | 435/94 |

*Primary Examiner*—Kenneth M. Schor
*Attorney, Agent, or Firm*—Vincent A. Mallare; Fred A. Wilson

[57] ABSTRACT

A method for producing L-sugars including L-idose and L-gulose as well as D-fructose from D-glucose. The method comprises epimerizing D-glucose to a mixture of D-glucose and D-mannose, hydrogenating the mixture in a fixed catalyst bed to provide D-sorbitol and D-mannitol, separating the D-mannitol by fractional crystallization, oxydizing separately the D-sorbitol and D-mannitol to provide L-sorbose and D-fructose, respectively; and racemizing the L-sorbose in a weak alkaline solution to provide a mixture of L-sorbose, L-idose and L-gulose, and precipitating the remaining L-sorbose with a dilute lime solution. The unconverted L-sorbose is recovered and recycled.

10 Claims, 1 Drawing Figure

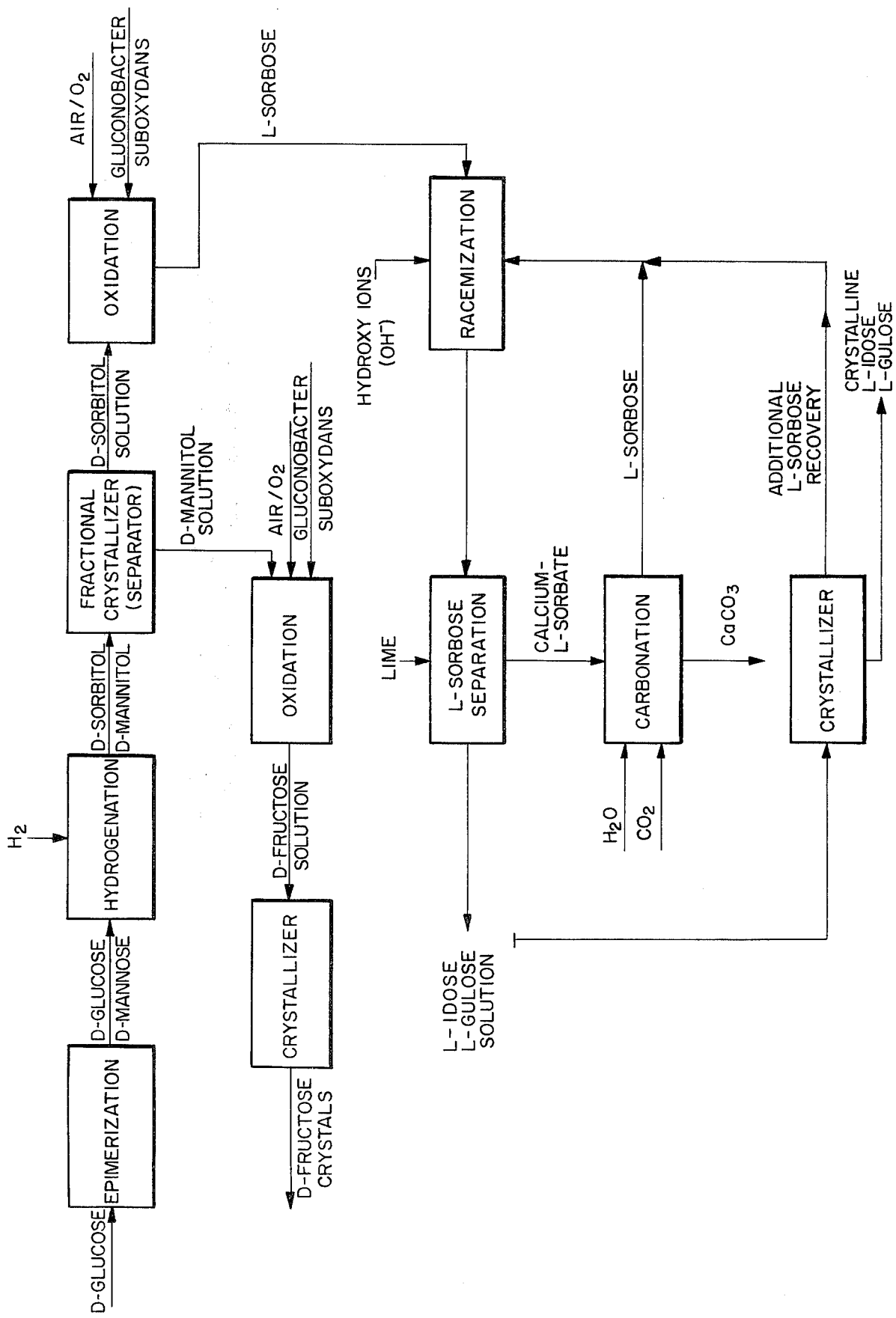

PROCESS FOR MAKING L-SUGARS AND D-FRUCTOSE

BACKGROUND OF THE INVENTION

This invention relates to L-sugars and more particularly to a method for commercially producing L-sugars as well as D-fructose for use as a sweetener for foodstuffs.

It has been known that sugars, i.e., D-sugars such as D-glucose, D-fructose and D-saccharose and others have been useful as sweeteners. According to U.S. Pat. No. 4,262,032, it is now known that the use of L-sugars, such as L-gulose may be used as sweeteners for foodstuffs and are non-calorific.

In U.S. Pat. No. 3,256,270, it is disclosed that D-glucose can be converted to D-fructose by treating the D-glucose with an aluminate. D-glucose, as disclosed by V. Bilik, Chem. Zvesti 26 183–186 (1972) can be epimerized by using molybdic acid as a catalyst. According to V. Bilik, 25% of D-glucose can be converted to D-mannose in this manner. Also, according to W. M. Kruse (ICI United States), German patent application No. 2,622,316 (Feb. 12, 1976), it was found that 50% of D-glucose can be epimerized to D-mannose with 0.25 to 1.0 W % molybdic acid catalyst provided the D-glucose concentration is increased to 67 W %-70 W %, at a temperature to 100° to 125° C., and a pH of 3 to 5, in 30 to 120 minutes. In these reactions, after they are completed, the molybdic acid has to be removed with an anion exchange resin, after dilution of the mixture to 50 W %.

The production of L-sugars has generally been done experimentally in the laboratory and not on a commercial basis. However, since there is a need for producing sugars which are non-calorific, it would be advantageous to provide a method which would provide L-sugars such as those provided by the present invention, both economically and efficiently.

SUMMARY OF THE INVENTION

The present invention provides a method for producing L-sugars including L-idose and L-gulose as well as D-fructose from D-glucose. The method comprises the steps of epimerizing D-glucose to a mixture of D-glucose and D-mannose, hydrogenating the mixture in a fixed catalyst bed to provide D-sorbitol and D-mannitol, separating the D-sorbitol from the D-mannitol, oxidizing the D-sorbitol to provide L-sorbose, converting the L-sorbose in a weak alkaline solution to provide a mixture of L-idose and L-gulose and precipitating L-sorbose with a dilute lime solution. The D-mannitol is separately oxidized to D-fructose.

BRIEF DESCRIPTION OF THE DRAWING

The present invention will be understood more clearly by considering the following description in conjunction with the drawing, wherein:

FIG. 1 is a flow diagram of a process for preparing L-sugars and D-fructose according to the present invention.

DETAILED DESCRIPTION OF THE PREFERRED EMBODIMENT

Referring to FIG. 1, there is illustrated by means of a flow diagram, a process for preparing L-sugars such as L-idose and L-gulose as well as D-fructose. The L-sugars are the mirror image of corresponding D-sugars, e.g., L-idose is the mirror image of D-idose.

In FIG. 1, it is shown that the L-sugars and D-fructose are generally produced from the basic material, D-glucose. According to the present process, an aqueous solution of D-glucose is first epimerized to a mixture of D-glucose and D-mannose, preferably in a fixed catalyst bed. This mixture is then hydrogenated to provide a mixture of D-sorbitol and D-mannitol, from which the D-mannitol is removed by cooling and fractional crystallization.

The D-sorbitol, in solution, is then treated with oxygen or air in the presence of oxydizing microbes, i.e., *Gluconobacter suboxydans,* which are also referred to as *Acetobactor suboxydans.* The D-sorbitol after being oxygenated, provides L-sorbose which is treated, i.e., racemized, by addition of an alkaline substance (i.e., hydroxy ion) and converted to a mixture of L-sorbose, L-idose and L-gulose. In this conversion, there is an equilibrium which is established where all three isomers are present. This racemization reaction proceeds readily at temperatures of from about 20° to about 80° C.; temperatures ranging from about 25° to about 60° C. being preferable. The reaction time at 25° to 35° C. varies from 56 to 14 hours, but at higher temperatures the racemization proceeds faster. The unconverted L-sorbose is recycled.

The remaining L-sorbose is precipitated from the mixture in the separation step with lime from a dilute aqueous solution, i.e., a 6 to 7% solution and then cooled. This precipitation utilizes the principles of "Steffan's Process" in which sucrose is separated by means of a lime salt known as calcium saccharate. In the present process, the L-sugars mixture is diluted to 6 to 7 percent and cooled to 18° C. Finely pulverized lime is added with agitation to form a precipitate of calcium L-sorbate. This precipitate (containing about 90% of L-sorbose) is filtered. The filtrate is heated, during which another precipitation occurs and this too is filtered. Cold L-sorbate precipitate is removed by vacuum filtration, and hot precipitate by a thickener. Both precipitates are mixed with water and carbonated where lime L-sorbate is decomposed into calcium carbonate ($CaCO_3$) and L-sorbose which is recycled.

The solution of L-idose and L-gulose from which the L-sorbose was precipitated, is passed from the separation step to a fractional crystallizer. From the crystallizer, crystalline L-sugars, i.e., L-idose and L-gulose, are provided. Also, from the crystallizer, additional L-sorbose is recovered and recycled.

As shown in FIG. 1, D-mannitol can be treated to produce D-fructose. Accordingly, the D-mannitol separated from the D-sorbitol by fractional crystallization is treated with oxygen or air in the presence of oxidizing microbes, i.e., *Gluconobacter suboxydans* to produce a D-fructose solution. The D-fructose solution is then passed through a crystallizer to provide D-fructose crystals.

The epimerization process, where D-mannose is produced, uses a 40 to 70% aqueous glucose solution and most preferably, a 65 to 70% aqueous D-glucose solution at 100°–125° C., having a pH of 3–5. The reaction time of the process is from about 30 to 120 minutes.

Also, in place of the pure D-glucose, solutions of crude starch hydrolyzate can be used for producing the D-sorbitol, D-mannitol and eventually the L-sugars, i.e., L-idose and L-gulose, and D-fructose.

The catalyst of the fixed bed in which the D-glucose is epimerizing is preferably silicontungstic acid or silicagel. There are other catalysts which may be used in this hydrogenation process, which include molybdic acid on silicagel, phophomolybidc acid on silicagel, and similar derivatives of molybdenum and tungsten, on a silicagel that is preferably acid washed.

In the present process, the intermediates D-sorbitol and D-mannitol should be noted since D-sorbitol and D-mannitol are quite costly to manufacture. However, it has been found according to the process disclosed in U.S. Ser. No. 258,225 that D-sorbitol can be economically produced. Accordingly, the present disclosure includes by reference the process disclosed in U.S. Ser. No. 285,225; filed Apr. 27, 1981.

In the hydrogenation of D-glucose and D-mannose with the fixed catalyst bed, the hydrogen flow rate is related to the liquid feed rate and by the quantity of catalyst used, as the hydrogen gas flow provides for carrying the feed liquid droplets through the fixed-catalyst type beds to achieve intimate contact with the catalyst particles. The liquid feed rate in the present hydrogenation ranges from about 0.3 to about 10.0 g./hr./g. of catalyst, and preferably from about 0.4 to about 8.0 g./hr./g. of catalyst. Accordingly, the ratio of hydrogen gas to liquid feed rate at standard conditions ranges from about 500 to about 5000 for achieving satisfactory conversion of D-glucose to D-sorbitol.

Th aerobic fermenting bacteria include: *Gluconobacter oxydans* (subsp. suboxydans). The amount of suboxydans used is generally related to the amount of the D-sorbitol or D-mannitol fed. This latter amount ranges from about 20 g to about 80 g./hr./g. of catalyst. D-sorbitol yields L-sorbose and D-mannitol yields D-fructose.

In the conversion of the L-sorbose in a weak alkaline solution, this solution may be a 1.0 N solution of hydroxide such as sodium hydroxide or calcium hydroxide.

The conditions under which the D-glucose is hydrogenated to D-sorbitol in the fixed catalyst bed is at a temperature ranging from about 100° to about 150° C. and a pressure ranging from about 500 to about 2000 psig hydrogen partial pressure.

The conversion of L-sorbose to the L-sugars takes place generally at a temperature ranging from about 20° to about 80° C.

The L-sugars, i.e., L-idose and L-gulose, may be utilized as a sweetening material for foodstuffs of all kinds. The L-sugars are a sweetening agent which are non-calorific and less susceptible to spoilage due to the growth of various micro-organisms than those prepared with conventional saccharide sweetening agents. For example, one real problem associated with the use of formations such as syrups that are prepared from conventional saccharide sweeteners such as in soft drinks, is the decomposition due to bacterial growth. Since the L-hexose sweetening agents, i.e., L-sugars, of the present invention provide little or no nutrient value for the various micro-organisms, their growth and, hence, the corresponding spoilage of these formations is drastically reduced.

I claim:

1. A method for producing L-sugars including L-idose and L-gulose and D-fructose from D-glucose which comprises the steps of:
   (a) epimerizing D-glucose to a mixture of D-glucose and D-mannose;
   (b) hydrogenating said D-glucose mixture to provide L-sorbitol and D-mannitol;
   (c) separating said D-mannitol from said D-sorbitol;
   (d) oxidizing separately said D-sorbitol and D-mannitol to provide L-sorbose and D-fructose, respectively;
   (e) racemizing said L-sorbose to provide a mixture of L-sorbose, L-idose and L-gulose; and
   (f) precipitating the remaining L-sorbose with lime from a dilute solution of said mixture of L-sorbose, L-idose, and L-gulose.

2. The method according to claim 1, wherein the epimerization of said D-glucose takes place in a fixed catalyst bed of silicotungstic acid or silicagel.

3. The method according to claim 1, wherein any unconverted L-sorbose is recycled.

4. The method according to claim 1, wherein said D-glucose is a 10 to 70% aqueous solution.

5. The method according to claim 1, wherein said mixture of D-glucose and D-mannose is hydrogenated in a fixed catalyst bed at a temperature ranging from about 100° to about 150° C.

6. The method according to claim 1, wherein said L-sorbose is precipitated in a 6 to 7% lime solution.

7. The method according to claim 1, wherein said L-sorbose is racemized in a 1.0 N alkaline solution.

8. The method according to claim 1, wherein the oxidation of L-sorbose is carried out with an oxygen containing gas in the presence of *Gluconobacter suboxydans*.

9. The method according to claim 1, wherein the oxidation of D-mannitol to D-fructose is carried out with an oxygen containing gas in the presence of *Gluconobacter suboxydans*.

10. The method according to claim 1, wherein the L-idose and L-gulose are recovered by crystallization after removal of the L-sorbose with lime.

* * * * *